United States Patent [19]
Lunnen et al.

[11] Patent Number: 6,025,179
[45] Date of Patent: Feb. 15, 2000

[54] METHOD FOR CLONING AND PRODUCING THE SNABI RESTRICTION ENDONUCLEASE AND PURIFICATION OF THE RECOMBINANT SNABI RESTRICTION ENDONUCLEASE

[75] Inventors: Keith D. Lunnen, Essex; Huimin Kong, Wenham; Geoffrey G Wilson, Beverly, all of Mass.

[73] Assignee: New England Biolabs, Inc., Beverly, Mass.

[21] Appl. No.: 09/143,776

[22] Filed: Aug. 31, 1998

[51] Int. Cl.[7] ............................. C12N 9/22; C12N 15/55
[52] U.S. Cl. ................... 435/199; 435/252.3; 435/320.1; 536/23.2
[58] Field of Search ................... 435/199, 320.1, 435/252.3; 536/23.2

[56] References Cited

U.S. PATENT DOCUMENTS

| | | | |
|---|---|---|---|
| 5,200,333 | 4/1993 | Wilson | 435/172.3 |
| 5,246,845 | 9/1993 | Wilson et al. | 435/172.3 |
| 5,498,535 | 3/1996 | Fomenkov et al. | 435/172.3 |

OTHER PUBLICATIONS

Roberts et al., Nucl. Acids Res. 26:338–350(1998).
Kosykh et al., Mol. Gen. Genet. 178:717–718 (1980).
Mann et al., Gene 3:97–112 (1978).
Walder et al., Proc. Nat. Acad. Sci. 78:1503–1507 (1981).
Bougueleret et al., Nucl. Acids Res. 12:3659–3676 (1984).
Gingeras et al., Proc. Natl. Acad. Sci. USA 80:402–406 (1983).
Theriault et al., Gene 19:355–359 (1982).
Blumenthal et al., J. Bacteriol. 164:501–509 (1985).
Kiss et al., Nucl. Acids Res. 13:6403–6421 (1985).
Szomolanyi et al., Gene 10:219–225 (1980).
Janulaitis et al., Gene 20:197–204 (1982).
Kiss et al., Gene 21:111–119 (1983).
Walder et al., J. Biol. Chem. 258:1235–1241 (1983).
Fomenkov et al., Nucl. Acids Res. 22:2399–2403 (1994).
Brooks et al., Nucl. Acids Res. 19:841–850 (1991).
Tao et al., J. Bacteriol.173:1367–1375 (1991).
Skoglund et al., Gene 88:1–5 (1990).
Yanisch–Perron et al., Gene 33:103–119 (1985).
Kong et al., Nuc. Acids Res. 18:2832 (1990).
Yang, et al., Nuc. Acids Res. 18:3083 (1990).

*Primary Examiner*—Charles L. Patterson, Jr.
*Attorney, Agent, or Firm*—Gregory D. Williams

[57] ABSTRACT

The methylase selection method was used to clone the SnaBI methylase gene (snaBIM) from *Sphaerotilus natans* (ATCC 15291). An active SnaBI methylase was cloned in *E. coli* using pSnaBI-2, a pUC19 derivative containing two SnaBI sites. Because methylase and restriction genes are usually located alongside each other in a restriction-modification systems, efforts were made to clone the downstream DNA by inverse PCR. Inverse PCR cloned the missing portion of the SnaBI endonuclease and also identified a control, or C, protein. The two open reading frames snaBIR (ORF1) and snaBIC (ORF2) converged toward the SnaBI methylase gene (ORF). Attempts to establish a snaBIR-recombinant plasmid expressing the SnaBI endonuclease in *E.coli* modified with SnaBI methylase failed. Overexpression of the SnaBI endonuclease in *E. coli* required the use of the heterospecific BsaAI methylase.

6 Claims, 3 Drawing Sheets

SnaBIM

```
        ATGTTTTACTACTACGGCAGAAAAAAACAAATCGCAAAGCATTATCCGGCTCCAAATTAT
  1     ---------+---------+---------+---------+---------+---------+
        M  F  Y  Y  Y  G  R  K  K  Q  I  A  K  H  Y  P  A  P  N  Y
        GGATGCATAATTGAGCCATTTGCGGGATCCGCCGCCTACTCACTCTTCTCAGGCAACTGG
  61    ---------+---------+---------+---------+---------+---------+
        G  C  I  I  E  P  F  A  G  S  A  A  Y  S  L  F  S  G  N  W
        CGCAATCAAGTCGTTTTAATTGAAAAAGACCCCAAAGTCGCATCCATTTGGGAGTGGTTG
  121   ---------+---------+---------+---------+---------+---------+
        R  N  Q  V  V  L  I  E  K  D  P  K  V  A  S  I  W  E  W  L
        ATAAGCGAAGCGACTGAACAAAAAATCAAAAACCTGCCAGACCTGAAGGTTGGAGAAAAA
  181   ---------+---------+---------+---------+---------+---------+
        I  S  E  A  T  E  Q  K  I  K  N  L  P  D  L  K  V  G  E  K
        AGTTCAGAGTTCCTTCACATTATTCATGCGGCCACAAAAATGGCATTCAAATACAAAACC
  241   ---------+---------+---------+---------+---------+---------+
        S  S  E  F  L  H  I  I  H  A  A  T  K  M  A  F  K  Y  K  T
        ATAACGGTTACCCCAGTTTTGGCTAGAAACTGGGAAATTAGCAGGCGCGTTATGGCCGAA
  301   ---------+---------+---------+---------+---------+---------+
        I  T  V  T  P  V  L  A  R  N  W  E  I  S  R  R  V  M  A  E
        AACCTGCAAAAAATTAAACATTGGCAAATAATTTGCGGAGACTACACAGTGGCTCCTGAT
  361   ---------+---------+---------+---------+---------+---------+
        N  L  Q  K  I  K  H  W  Q  I  I  C  G  D  Y  T  V  A  P  D
        ATTGAGGCTACTTGGTTTATTGATCCGCCATACAAGTCAGAGCCAGGAATGGGTTACGGC
  421   ---------+---------+---------+---------+---------+---------+
        I  E  A  T  W  F  I  D  P  P  Y  K  S  E  P  G  M  G  Y  G
        TTCAGCAGTGCACTTATCAACTACGAGGAACTGGCAAAATGGAGCCTAAACAGGCAGGGA
  481   ---------+---------+---------+---------+---------+---------+
        F  S  S  A  L  I  N  Y  E  E  L  A  K  W  S  L  N  R  Q  G
        GAAGTAATTTGCTGCGAGGGTGAGTATGGCGACTACCTGCCATTTGAAACTCTGCTGGAT
  541   ---------+---------+---------+---------+---------+---------+
        E  V  I  C  C  E  G  E  Y  G  D  Y  L  P  F  E  T  L  L  D
        TTAAAGGGCGTTGCGGGAAAGTCAAGCAGGGAAAAAATATTTTACCGCACGCCACATTCG
  601   ---------+---------+---------+---------+---------+---------+
        L  K  G  V  A  G  K  S  S  R  E  K  I  F  Y  R  T  P  H  S
        CCCATGCAACTCAGGCTAGTCGCGTAG
  661   ---------+---------+-------  687
        P  M  Q  L  R  L  V  A  *
```

FIG. 3

SnaBIR

```
     ATGCTGAATTACAAGATTAATCCAGGACTCCATATCAATTGCGGATTTATTGTTACTGGT
  1  ---------+---------+---------+---------+---------+---------+  60
      M  L  N  Y  K  I  N  P  G  L  H  I  N  C  G  F  I  V  T  G
     GAAGCCGTCCGCAATGCAATAATGCAAACGAATGCCATCCTTGGGGACTTGCCGGCAAAT
 61  ---------+---------+---------+---------+---------+---------+  120
      E  A  V  R  N  A  I  M  Q  T  N  A  I  L  G  D  L  P  A  N
     TTGTACAAAAGCATCGACTACAAAACGACTAGCGCAATGATTGGCTCCGTCTTTTGCGAC
121  ---------+---------+---------+---------+---------+---------+  180
      L  Y  K  S  I  D  Y  K  T  T  S  A  M  I  G  S  V  F  C  D
     AGGCTTGCTGATGTGGTTGGGGCAATTGTTAATCCTATTGAGAAGGGGCATCCTGATTTG
181  ---------+---------+---------+---------+---------+---------+  240
      R  L  A  D  V  V  G  A  I  V  N  P  I  E  K  G  H  P  D  L
     GTGCCTCCAGCAGCGATTAACTGCACCGAAGAGGAGTTACGGAACTACCCACAGGGGCTG
241  ---------+---------+---------+---------+---------+---------+  300
      V  P  P  A  A  I  N  C  T  E  E  E  L  R  N  Y  P  Q  G  L
     GAAATCAAGTGCACCATTGGCAGCATAGAAACTGGTGCAGACTTGCGAGCGGGTCAAACC
301  ---------+---------+---------+---------+---------+---------+  360
      E  I  K  C  T  I  G  S  I  E  T  G  A  D  L  R  A  G  Q  T
     CGCATTGAATCGTTGACTGGAATCACGTGGCAGGCCCATCACCGCGAAGTTGCCGAACTG
361  ---------+---------+---------+---------+---------+---------+  420
      R  I  E  S  L  T  G  I  T  W  Q  A  H  H  R  E  V  A  E  L
     CTTGGTTTGGTTTGGGATTTTTTTGAAGATGGCCGGGCCTTCAACTATCCAGCAATCAGC
421  ---------+---------+---------+---------+---------+---------+  480
      L  G  L  V  W  D  F  F  E  D  G  R  A  F  N  Y  P  A  I  S
     GGGGCGTTTTATAGCGATGATCTTTGCGAGGATGATTGGGGACAAATCAGCGGAACGAAT
481  ---------+---------+---------+---------+---------+---------+  540
      G  A  F  Y  S  D  D  L  C  E  D  D  W  G  Q  I  S  G  T  N
     GGTCGCAACACAAAAGTGAGCGCGATGGTGGCAAGCGGAAAAGCAAAAATGGGTAGAGGC
541  ---------+---------+---------+---------+---------+---------+  600
      G  R  N  T  K  V  S  A  M  V  A  S  G  K  A  K  M  G  R  G
     TGGGTTGCTGTGGTTGAAAAAGATGAATATTTAACAGCGTACTCCAGAATCTTGAGGTTT
601  ---------+---------+---------+---------+---------+---------+  660
      W  V  A  V  V  E  K  D  E  Y  L  T  A  Y  S  R  I  L  R  F
     AGATTTCCATGA
661  ---------+--  672
      R  F  P  *
```

FIG. 4

SnaBIC

```
     ATGAACTCACTGAGTACCGCCATAGCCCAAGCGTTAGTCAAATATCGTCATTTGTCACAC
  1  ---------+---------+---------+---------+---------+---------+
      M  N  S  L  S  T  A  I  A  Q  A  L  V  K  Y  R  H  L  S  H
     CTCTCTCAAGAGGAGCTTGCCGATGCTGCTGGCATTCATAGAACCTATGTGAGTCAGATA
 61  ---------+---------+---------+---------+---------+---------+
      L  S  Q  E  E  L  A  D  A  A  G  I  H  R  T  Y  V  S  Q  I
     GAGCGCGGGCTAAAGATGCCCACTGTCGCCATTCTTTTTAAAATTTCCAAGGCGCTGAAT
121  ---------+---------+---------+---------+---------+---------+
      E  R  G  L  K  M  P  T  V  A  I  L  F  K  I  S  K  A  L  N
     ATTCGAGCAAGCGACTTGATTGGTGAGATTGAAGGTCAGTATGCTGAATTACAAGATTAA
181  ---------+---------+---------+---------+---------+---------+ 240
      I  R  A  S  D  L  I  G  E  I  E  G  Q  Y  A  E  L  Q  D  *
```

FIG. 5

BsaAIM/pIH919

FIG. 6 pCAB16

Note: SnaBIR cloned at BsaAI site

FIG. 7

SnaBIR-pRRS

METHOD FOR CLONING AND PRODUCING THE SNABI RESTRICTION ENDONUCLEASE AND PURIFICATION OF THE RECOMBINANT SNABI RESTRICTION ENDONUCLEASE

BACKGROUND OF THE INVENTION

The present invention relates to recombinant DNA which encodes the SnaBI restriction endonuclease as well as SnaBI methylase, and to the production of SnaBI restriction endonuclease from the recombinant DNA.

Type II restriction endonucleases are a class of enzymes that occur naturally in bacteria. When they are purified away from other bacterial components, these restriction endonucleases can be used in the laboratory to cleave DNA molecules into small fragments for molecular cloning and gene characterization.

Restriction endonucleases act by recognizing and binding to particular sequences of nucleotides (the 'recognition sequence') along the DNA molecule. Once bound, they cleave the molecule within, to one side of, or to both sides of the recognition sequence. Different restriction endonucleases have affinity for different recognition sequences. Over two hundred restriction endonucleases with unique specificities have been identified among the thousands of bacterial species that have been examined to date (Roberts and Macelis, Nucl. Acids Res. 24:223–235 (1996)).

Restriction endonucleases are named according to the bacteria from which they are derived. Thus, the three different restriction endonucleases synthesized by *Deinococcus radiophilus,* for example, are named DraI, DraII and DraIII. These enzymes recognize and cleave the sequences 5'TTTAAA 3', 5'PuGGNCCPy3' and 5'CACNNNGTG3' respectively. Likewise, the single restriction endonuclease synthesized by *Escherichia coli* RY13 is termed EcoRI. It recognizes the sequence 5'GAATTC3'.

Restriction endonucleases generally occur together with a second enzyme, the modification methylase. Together, the two enzymes form bacterial restriction-modification (R-M) system. Methylases are complementary to restriction endonucleases and they provide a way for bacteria to protect their own DNA from self-digestion. Modification methylases recognize and bind to the same recognition sequence as the restriction endonuclease they accompany, but instead of cleaving the DNA, they chemically modify one of the nucleotides within the sequence by the addition of a methyl group to form 5-methylcytosine, $N^4$-methylcytosine, or $N^6$-methyladenine. Following this methylation, the recognition sequence is no longer cleaved by the cognate restriction endonuclease. The DNA of a bacterial cell is always fully modified by virtue of the activity of its modification methylase(s), and therefore it is completely insensitive to the presence of the endogenous restriction endonuclease(s). It is only unmodified, that is to say foreign, DNA that is sensitive to restriction endonuclease recognition and cleavage.

With the advent of recombinant DNA technology, it is possible to clone genes and overproduce the enzymes they encode in large quantities. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Restriction-modification systems are being cloned with increasing frequency. The first cloned systems used bacteriophage infection as a means of identifying or selecting restriction endonuclease clones (EcoRII: Kosykh et al., *Mol. Gen. Genet.* 178:717–719 (1980); HhaII: Mann et al., *Gene* 3:97–112 (1978); PstI: Walder et al., *Proc. Nat. Acad. Sci.* 78:1503–1507 (1981)). Since the presence of restriction-modification systems in bacteria enable them to resist infection by bacteriophages, cells that carry cloned restriction-modification genes can, in principle, be selectively isolated as survivors from libraries that have been exposed to phages. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acids. Res.* 12:3659–3676 (1984); PaeR7: Gingeras and Brooks, *Proc. Natl. Acad. Sci. USA* 80:402–406 (1983); Theriault and Roy, *Gene* 19:355–359 (1982); PvuII: Blumenthal et al., *J. Bacteriol.* 164:501–509 (1985)).

A third approach to clone R-M systems is by selection for an active methylase gene (U.S. Pat. No. 5,200,333 and BsuRI: Kiss et al., *Nucl. Acids. Res.* 13:6403–6421 (1985)). Since R and M genes are usually closely linked, both genes can often be cloned simultaneously. This selection does not always yield a complete restriction system however, but instead yields only the methylase gene (BspRI: Szomolanyi et al., *Gene* 10:219–225 (1980); BcnI: Janulaitis et al., *Gene* 20:197–204 (1982); BsuRI: Kiss and Baldauf, *Gene* 21:111–119 (1983); and MspI: Walder et al., *J. Biol. Chem.* 258:1235–124 (1983)).

Another approach to clone R-M Systems in *E. coli* makes use of the fact that certain modification genes, when cloned into a new host and adequately expressed, enable the host to tolerate the presence of a different restriction gene. (Wilson et al; U.S. Pat. No. : 5,246,845 (1993)).

A more recent method, the "endo-blue method", has been described for direct cloning of restriction endonuclease genes in *E. coli* based on the indicator strain of *E. coli* containing the dinD::lacZ fusion (Fomenkov et al., U.S. Pat. No. 5,498,535; Fomenkov et al., *Nucl. Acids Res.* 22:2399–2403 (1994)). This method utilizes the *E. coli* SOS response following DNA damages caused by restriction endonucleases or non-specific nucleases. A number of thermostable nuclease genes (Tth111I, BsoBI, Tf nuclease) have been cloned by this method (U.S. Pat. No. 5,498,535).

Because purified restriction endonucleases, and to a lesser extent, modification methylases, are useful tools for analyzing and rearranging DNA molecules in the laboratory, there is a strong commercial incentive to engineer bacterial strains that produce these enzymes in large quantities. Such overexpression strains increase the enzyme yield and simplify the task of enzyme purification.

SUMMARY OF THE INVENTION

The methylase selection method was used to clone the SnaBI methylase gene (snaBIM) from *Sphaerotilus natans* (ATCC 15291). Using an ApoI partial digest, an active SnaBI methylase was cloned in *E. coli* using plasmid vector pSnaBI-2 (a pUC19 derivative containing two SnaBI sites; one at the SspI site and another at a DraI site located between the Amp gene and the ori of pUC19). DNA sequencing verified the location of the inserted snaBIM gene and identified an incomplete converging open reading frame (ORF1).

Because methylase and endonuclease genes usually occur alongside each other in restriction-modification systems, efforts were made to clone the DNA flanking the snaBIM gene. Southern blots were used to identify adjacent DNA fragments for denovo cloning, and inverse PCR was used to isolate flanking DNA. Blotting revealed that AatII-, BamHI-, PstI-, SalI-, and SphI-fragments should contain snaBIM and sufficient enough adjacent DNA to include the SnaBI restriction gene (snaBIR) as well. Blots also identified a HincII fragment later used for inverse PCR. Methylase selection on de novo libraries prepared with AatII, BamHI, PstI, SalI and SphI, failed to yield SnaBI methylase clones. Attempts to obtain clones by tranforming selections into E.coli pre-modified by a plasmid containing the SnaBI methylase gene (snaBIM) also failed. After one round of inverse PCR, followed by directed PCR, adjacent chromosomal DNA was cloned into pUC19. Two open reading frames (ORFs) were found downstream of the SnaBI methylase gene. The first ORF (ORF1) did not match known proteins in the Genbank data base which is indicative of a potential restriction endonuclease. The second converging ORF (ORF2) was homologous to previously described control, or C, proteins. (Brooks et al.,*NAR* 19:841–850 (1991), Tao, et al., *J. Bacterial* 173:1367–1375 (1991)).

Attempts to clone an active SnaBI restriction gene (ORF1) into pRRS (Skoglund et al, *Gene,* 88:1–5 (1990)) by transforming into a pre-modified E.coli host containing the SnaBI methylase gene failed. Only one pRRS snaBIR clone, with reduced SnaBI endonuclease activity, was ever isolated from a SnaBI methylase pre-modified E. coli host.

Figure 6:
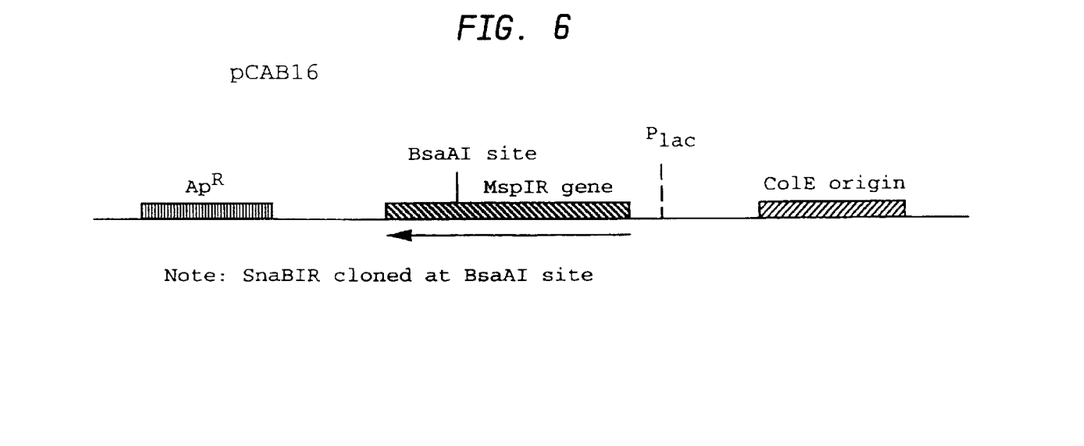
FIG. 6 illustrates a plasmid map of pCAB16.
Figure 7:
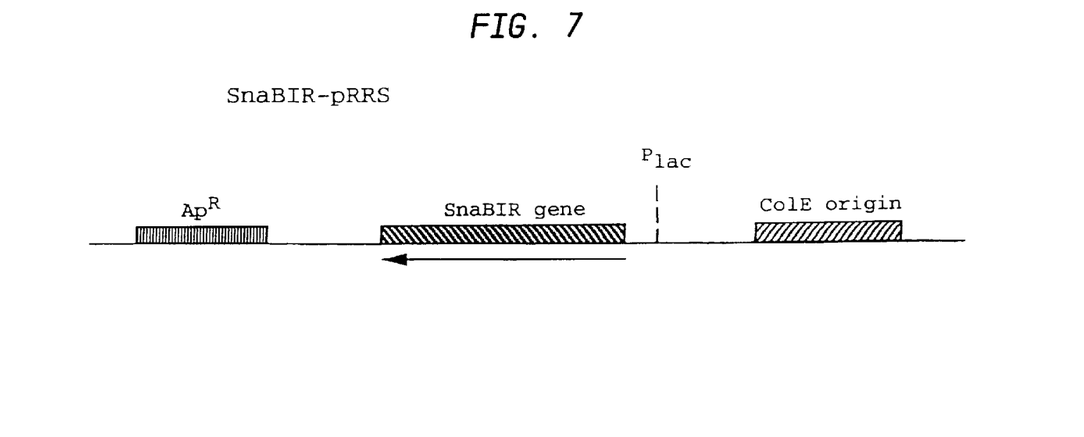
FIG. 7 illustrates a plasmid map of pRRS-SnaBIR endonuclease clone.

Using Vent® DNA polymerase, the snaBIR PCR fragment was then cloned and sequenced after ligation into pCAB16 at a BsaAI site (provided by Bill Jack and Lucia Greenough, New England Biolabs). pCAB16 is a pUC18 derivative containing the active mspIR gene cloned into the polylinker of pUC18 with mspIR transcribed from the Plac promoter. Interrupting pCAB16 at the BsaAI site interrupts mspIR expression, which would otherwise be lethal. This selects for inserts at the BsaAI site (FIG. 6). The snaBIR PCR fragment was ligated into pCAB16 and transformed into a SnaBI pre-modified E. coli host. Plasmid DNA was purified from fifteen isolates and digested with PstI and BamHI. Six isolates contained the PCR snaBIR fragment. Four of these, #1, #2, #4 and #9 were sequenced. Sequencing revealed that clones #2 and #4 contained mutations and that only clones #1 and #9 had the correct DNA sequence for snaBIR. All four clones were in the opposite orientation to Plac and mspIR, and when assayed, none of them showed detectable SnaBI restriction endonuclease activity.

The SnaBI endonuclease gene (snaBIR) fragments from #1 and #9 were gel purified following digestion with PstI and BamHI, and ligated separately into pRRS. To establish an overexpressor of R.SnaBI, it was then necessary to use an E.coli host pre-modified against SnaBI digestion. However, transforming these ligations into a host pre-modified with the SnaBI methylase failed to allow the establishment of an active SnaBI restriction clone except for one pRRS clone with reduced activity for SnaBI endonuclease. Of sixteen clones isolated, only one, #12, appeared to have the correct fragment, but when assayed showed reduced SnaBI endonuclease activity.

The SnaBI endonuclease recognizes the DNA sequence 5'TAC/GTA 3' and cleaves between the third and the fourth bases leaving blunt ends. Using the BsaAI methylase, a hetero-specific methylase that recognizes the DNA sequence 5' PyAC/GTPu 3', a highly expressing SnaBI endonuclease clone was established in E.coli. First, the BsaAI methylase gene (provided by Huimin Kong, New England Biolabs) was cloned onto pIH919, a derivative of pACYC184 containing the Plac promoter and polylinker from pUC18, and then transformed into E.coli. This M.BsaAI pre-modified E.coli strain protected against SnaBI digestion and perhaps against observed SnaBI endonuclease star activity. (Unpublished results, Paul Walsh, New England Biolabs) The pRRS ligations of #1 and #9 gel purified fragments were tranformed into the M.BsaAI pre-modified E.coli host and twelve colonies from each transformation were isolated. All 24 clones appeared to contain the correct insert. Six clones from each plate were sequenced and assayed for SnaBI endonuclease. All assayed clones expressed R.SnaBI at more than 8×10⁶ units of SnaBI endonuclease produced per gram of wet E.coli cells. All clones contained the correct snaBIR DNA sequence. The SnaBI endonuclease is purified from these clones by chromatography to near homogeneity.

BRIEF DESCRIPTION OF THE DRAWINGS

FIG. 3 is the SnaBI endonuclease gene (SEQ ID NO:3) and its encoded amino acid sequence (SEQ ID NO:4).

FIG. 4 is the SnaBI control gene (SEQ ID NO:5) and its encoded amino acid sequence (SEQ ID NO:6).

DETAILED DESCRIPTION OF THE INVENTION

In order to overproduce the SnaBI endonuclease from a clone, additional steps beyond the customary methylase selection procedure are required including the use of a heterospecific methylase, M.BsaAI, to protect E. coli DNA from SnaBI digestion. A plasmid containing bsaAIM is first used to modify an E. coli host. This host is then transformed with a compatible plasmid containing the snaBIR gene, pRRS+snaBIR, followed by selection for colonies that contain both plasmids on antibiotic plates. The gene encoding M.BsaAI has been described.

The method described herein by which the SnaBI methylase gene and the SnaBI restriction endonuclease genes are preferably cloned and expressed in E. coli employs the following steps:

1. Construction of an ApoI partial genomic DNA library.

*Sphaerotilus natans* genomic DNA was incubated with ApoI to achieve partial digestion. The ApoI partially digested genomic DNA in the range of 0.5–20 kb was ligated into EcoRI-cut and CIP-treated vector pSnaBI-2 at 17° C. overnight. The ligated DNA was transformed into E. coli RR1 competent cells. The transformants were plated, pooled and amplified. Plasmid DNA was prepared from overnight cell cultures of the pools.

2. Challenge the ApoI partial library DNA with SnaBI digestion and isolate the of SnaBI methylase gene.

The ApoI partial library DNA was digested with SnaBI at 37° C. overnight. The digested DNA was precipitated and de-phosphorylated by treatment with CIP followed by transformation into RR1 competent cells. Plasmid DNA was isolated from twenty-eight transformants. Individual plasmid DNAs were digested with SnaBI to detect any resistance to digestion. One plasmid isolate, #18, displayed resistance to SnaBI digestion. The degree of resistance to SnaBI digestion was complete.

3. Sequencing of the insert carrying the SnaBI methylase gene.

The entire ApoI fragment insert in plasmid #18 was sequenced. The insert was found to be 1264 bp in length and to encode one complete open reading frame (ORF) and one incomplete converging open reading frame (ORF1). When the complete ORF was compared to the known gene products in GenBank using BLAST, it showed extensive homology to $N^6$-methyladenine methylases. The complete ORF (687 bp) thus encodes the SnaBI methylase (228 aa. molecular mass =26.1 kDa).

4. Inverse PCR to clone the missing portion of the snaBIR and indentification of snaBIC.

*Sphaerotilus natans* genomic DNA was amplified by inverse PCR. The inverse PCR product was gel-purified from self-ligated HincII-cleaved DNA. The inverse PCR product was digested with ApoI and XbaI, cloned into pUC19 cut with ApoI and XbaI, and sequenced. 371 bp of new sequence was obtained. A new ApoI site was discovered outside the original cloned DNA on the chromosome of Sphaerotilus natans DNA. The HincII inverse PCR fragment was shortened to this ApoI site, and contained DNA from this ApoI site out to the HincII site. The cloned ApoI-XbaI fragment contained an ATG start codon and fifty-four codons of a new incomplete ORF (ORF2) converging toward the original cloned ApoI fragment. The rest of the new DNA from the HincII inverse PCR fragment was lost due to this newly discovered ApoI site in the adjacent chromosomal DNA. When ORF2 was compared to known proteins in GenBank using BLAST, it showed close homology to previously described control, or C, proteins (Brooks et al.,NAR 19:841–850, (1991), Tao, et al., *J. Bacterial* 173:1367–1375, (1991)).

Figure 1:
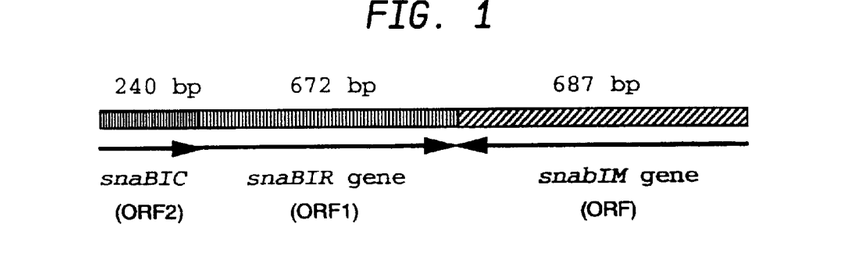
FIG. 1 illustrates the gene organization of SnaBI restriction-modification system.

ORF2 was assumed to be a new control gene (snaBIC) for the SnaBI R-M system. Since C genes usually precede restriction genes, we reasoned correctly that the SnaBI endonuclease gene was located downstream of snaBIC converging toward the original ApoI fragment containing snaBIM. PCR primers were then designed to PCR across this missing sequence back toward the original ApoI fragment containing snaBIM and the incomplete ORF1. The PCR product was digested with BamHI, cloned into pUC19 cut with SmaI and BamHI, and then sequenced. The newly-derived sequence extended the total DNA sequenced to 1805 bp and included sequence from the original methylase isolate #18, and the inverse PCR of the HincII chromosomal fragment. Translation of this DNA sequence in six reading frames indicated that there were two complete open reading frames downstream and converging toward the SnaBI methylase gene. The two ORFs overlap by 20 bases (see FIG. 1 for gene organization). The first ORF (ORF1) did not match with known proteins in the Genebank data base which is indicative of a potential restriction endonuclease. The second converging ORF (ORF2) was homologous to previously described control genes, or C, proteins.

5. Expression of SnaBI methylase gene in *E. coli*.

The entire SnaBI methylase gene (687 bp) was PCR amplified from genomic DNA using Vent® polymerase and two primers to snaBIM. The PCR product was digested with PstI and XmaI and ligated into pIH919 digested with PstI and XmaI followed by transformation into *E.coli* strain ER2267. Colony PCR was performed on eight colonies; two isolates, #3 and #8, contained the snaBIM PCR fragment and both were completely modified against SnaBI digestion. #8 was then transformed into *E.coli* strain ER2683 and made competent using the standard $CaCl_2$ method.

6. Expression of BsaAI methylase gene in *E. coli*.

A 1.4 kb SspI fragment containing the bsaAIM methylase gene was gel purified, ligated into the SmaI site of the CIP-treated vector, pIH919, and then transformed into *E.coli* ER2502. Plasmid DNA was purified from sixteen colonies; one clone, #8, contained the 1.4 kb SspI fragment. By co-transforming with pSnaBI-2 (a pUC19 derivative containing two SnaBI sites), the pIH919-bsaAIM isolate #8 was shown to fully protect pSnaBI-2 from SnaBI digestion. BsaAI methylase clone #8 was then transformed into *E.coli* strain ER2683 and made competent using the standard $CsCl_2$ method.

7. Cloning of complete SnaBI restriction endonuclease gene.

Two primers were synthesized for PCR amplification of snaBIR (ORF1). The PCR product was digested with PstI and BamHI and then ligated into PstI and BamHI digested pRRS. ER2683 [pIH919-snaBIM] and ER2683 [pIH919-bsaAIM] cells were then tranformed.

Both *E. coli* strains protected against SnaBI digestion, however only ER2683 [pIH919-bsaAIM] cells yielded a clone with SnaBI endonuclease activity from direct *Spaerotilus natans* chromosomal PCR. One clone out of twelve isolates, #33 from ER2683 [pIH919-bsaAIM] cells showed reduced endonuclease activity. ER2683 [pIH919-snaBIM] yielded no SnaBI endonuclease clones by direct SnaBI chromosomal PCR of the snaBIR gene.

The above undigested PCR of snaBIR (ORF1) was then ligated into pCAB16 at the BsaAI site followed by tranformation into ER2502 [pIH919-snaBIM] competent *Ecoli* cells. Plasmid DNA from fifteen isolates were purified and digested with PstI and BamHI. Six isolates contained the PCR generated snaBIR fragment. Four isolates, #1, #2, #4 and #9 were sequenced. Sequencing revealed that clones #2 and #4 contained mutations and that only clones #1 and #9 had the correct DNA sequence for snaBIR. All isolated clones were in the opposite orientation to Plac and mspIR, and all assayed clones of snaBIR PCR, including #1 and #9 showed no detectable SnaBI restriction endonuclease activity.

8. Expression of SnaBI endonuclease gene in *E. coli* strain ER2683 [pIH919-snaBIM].

Since #1 and #9 pCAB16-snaBIR clones contained flanking PstI and BamHI sites designed within the PCR primers, both plasmids were digested with PstI and BamHI, the snaBIR insert was gel purified and ligated into PstI and BamHI-digested pRRS inline with Plac promoter. This ligation reaction was again transformed into ER2683 [pIH919-snaBIM] *E. coli* cells as described section 7 for direct chromosomal PCR cloning attempt of snaBIR.

After transformation into *E.coli* ER2683 [pIH919-snaBIM], plasmid DNA was purified from sixteen colonies, eight from each #1 and #9 above ligations. In parallel, plasmid DNA from twelve colonies from a direct chromosomal PCR of snaBIR +pRRS transformation of ER2683 [pIH919-snaBIM] were also purified. Plasmid DNA was digested with PstI and BamHI to indentify the snaBIR insert; potential clones from each ligation were then assayed for SnaBI endonuclease activity. Only one isolate, #12, [from #9-pCAB16, gel pure PstI/BamHI snaBIR+ pRRS ligation], showed reduced activity of less than $5 \times 10^5$ units per gram. There were no clones with SnaBI endonuclease activity from the direct chromosomal snaBIR + pRRS ER2683 [pIH9l9-snaBIM] transformation.

9. Over-expression of SnaBI endonuclease gene in E. coli strain ER2683 [pIH919-bsaAIN].

Our failure to isolate clones overexpressing SnaBI endonuclease was judged to be a consequence of inadequate protection provided by the M.SnaBI methylase. This problem was solved by using the M.BsaAI methylase instead.

Figure 5:
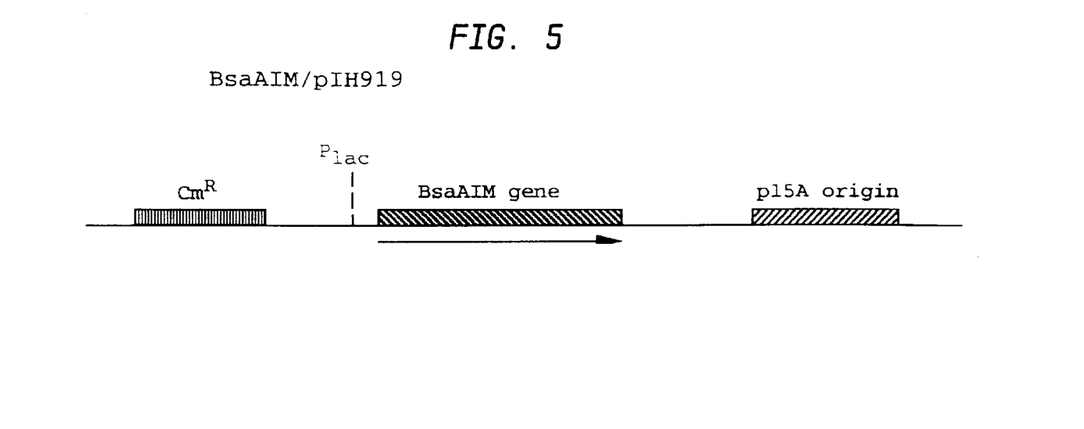
FIG. 5 illustrates a plasmid map of pIH919-BsaAI methylase clone.

We found that in order to successfully overproduce SnaBI endonuclease from a clone, the use of a heterospecific M.BsaAI methylase containing E.coli strain was essential (FIG. 5). As described in section 8, this same ligation [snaBIR +pRRS] from #1 and #9 pCAB16 snaBIR clones was transformed into competent E.coli strain ER2683 [pIH919-bsaAIM]. Twelve colonies from each transformation were isolated. All 24 clones contained the correct size insert. Six clones, #1, #2, #6, #13, #15, #18, displayed high activity for SnaBI endonuclease from overnight cultures. Cell extracts were assayed on T7 DNA for SnaBI endonuclease activity at 37° C. for 15 minutes and 1 hr. The enzyme activity yield is about $8\times10^6$ units/gram of wet E. coli cells.

10. Purification of SnaBI restriction endonuclease.

The recombinant SnaBI endonuclease was purified by standard protein purification techniques including ion-exhange chromatography The present invention is further illustrated by the following Examples. These Examples are provided to aid in the understanding of the invention and are not construed as a limitation thereof.

The references cited above and below are herein incorporated by reference.

EXAMPLE 1

CLONING OF SnaBI RESTRICTION-MODIFICATION SYSTEM IN E. coli

Genomic DNA was prepared from Sphaerotilus natans (ATCC 15291), NEB Culture Collection #308, (Borsetti el, New England Biolabs, unpublished observations).

1. Construction of a ApoI partial genomic DNA library.

2.5 µg of Sphaerotilus natans genomic DNA was digested with 8, 4, 2, 1, 0.5, 0.25, 0.125, and 0.05 units of ApoI at 50° C. for 60 min. 0.125 and 0.05 units of digestion gave rise to the desired degree of partial digestion. This ApoI partially digested genomic DNA in the range of 0.5–20 kb was incubated at 80° C. for 20 minutes. The genomic DNA was ligated into EcoRI-cut and CIP-treated vector pSnaBI-2 at 17° C. overnight. pSnaBI-2 contains a SnaBI linker; (5'GTACGTAC)3' 8 mer), at two different sites in pUC19 (Yanisch-Perron et al Gene 33:103–119(1985)): one at the SspI site and another at a DraI site between the Amp gene and ori Transformation was carried out by mixing RR1 (TonA−, DnaseI−) competent cells and the ligated DNA by the standard procedure. Transformants were plated on LB agar plus Amp (100 µg/ml). About 5000 colonies were obtained from this transformation. To increase the number of colonies, a 4X tranformation was again carried out using RR1 (TonA−, DnaseI−) cells and ligated DNA, and approximately 25,000 transformants were obtained. The transformants were pooled, inoculated into 500 ml of LB broth plus Amp, and incubated at 37° C. overnight. Plasmid DNA was prepared from this overnight culture by CsCl centifugation.

2. SnaBI digestion of the ApoI partial library DNA and cloning of SnaBI methylase gene.

1 µg of the ApoI partial library DNA was digested with 12 units of SnaBI at 37° C. overnight. The digested DNA was precipitated and de-phosphorylated by treatment with Calf Intestinal Phosphatase (CIP) followed by transformation of RR1 competent cells. One hundred and twenty transformants were obtained. Plasmid DNA was isolated from 10 ml cell cultures of 28 transformants and digested with 8 units of SnaBI at 37° C. for 2 hours to assay resistance to digestion. One plasmid isolate, #18, displayed complete resistance to SnaBI digestion. Restriction digestion of #18 plasmid DNA with ApoI indicated that it contains an insert of approximately 1.2 kb DNA.

3. Sequencing of the insert carrying the SnaBI methylase gene.

Figure 2:
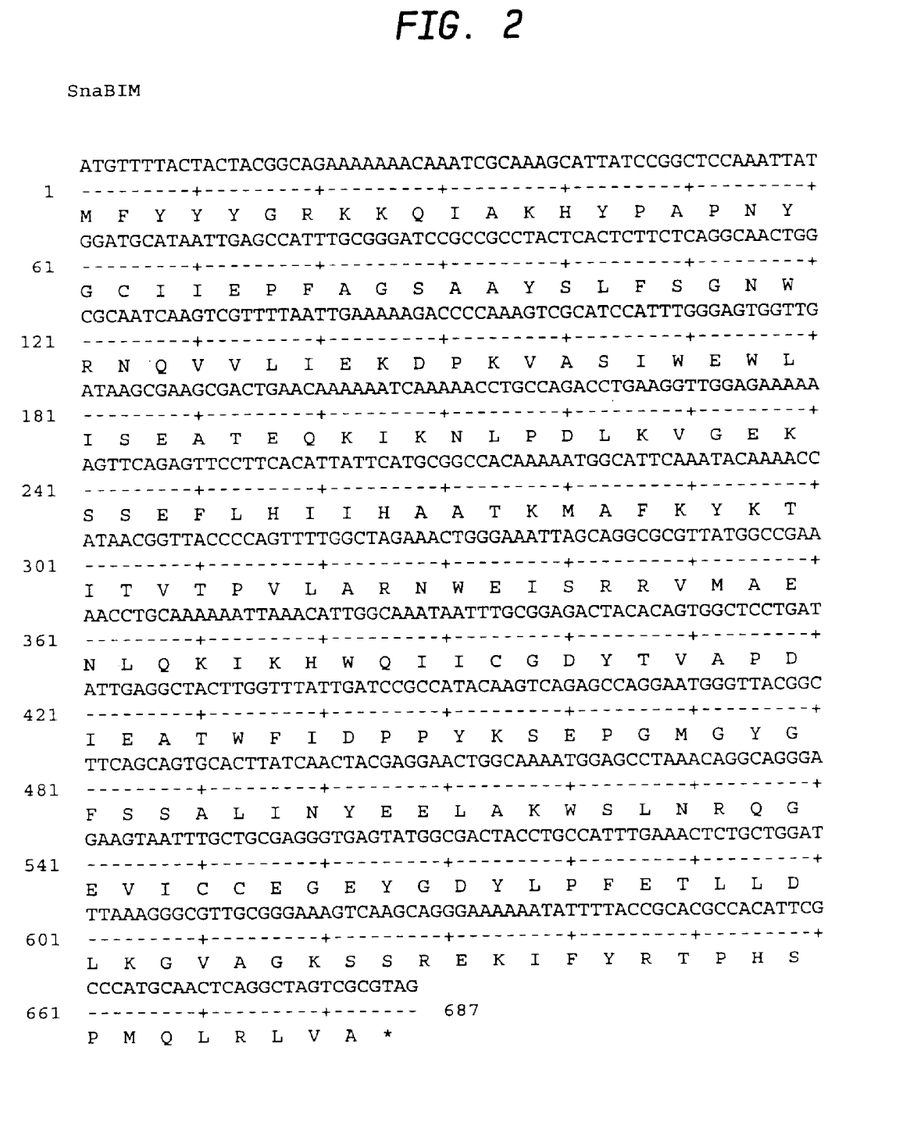
FIG. 2 is the SnaBI methylase gene (SEQ ID NO:1) and its encoded amino acid sequence (SEQ ID NO:2).

The insert of #18 plasmid DNA was sequenced by primer walking by the dideoxy termination method using an Ampli Taq DNA polymerase dye deoxy terminator sequencing kit and an ABI373A automated DNA sequencer. The entire insert, 1264 bp in length, encodes one complete open reading frame (ORF), and one incomplete converging open reading frame (ORF1). The nucleotide sequence analysis revealed that the complete ORF is the snaBIM gene. It is 687 bp in length and codes for a 228 aa protein of predicted MW of 26.1 kD. The M.SnaBI methylase aa sequence contains conserved motifs found in alpha type $N^6$-methyladenine methylases (FIG. 2).

4. Inverse PCR to clone the missing portion of snaBIR and identification of snaBIC.

To clone the missing portion of the SnaBI endonuclease (ORF1), the appropriate section of Sphaerotilus natans genomic DNA was amplified by inverse PCR. Sphaerotilus natans genomic DNA was cleaved with HincII. The cleaved DNA was self-ligated at a low concentration (2 µg/ml), and the ligated mixture was used as templates in inverse PCR using a set of primers:

5' TTCTCTAGAAGCTTGGGAGCGGGT-CAAACCCGC 3' (SnaBI1) (SEQ ID NO:7)

5' TTCGGATCCCCGGGCTCTCGGAGCCAAT-CATTGCGC3' (SnaBI2) (SEQ ID NO:8)

Using Vent® (Exo-) polymerase and the following cycling conditions of 95° C. 1' 60° C. 1', 72° C. 3.5', 30 cycles, an inverse PCR product of approximately 600 bp was generated. 1 µg of this 600 bp PCR product was then used as the DNA template in a second round of PCR amplification (100 µl reactions, 95° C. 1'55° C. 1', 72° C. 3.5', 30 cycles, Vent® (Exo+) polymerase) to generate more of the same 600 bp PCR fragment. Gel purified 600 bp PCR fragment was digested with ApoI and XbaI, ligated to ApoI- and XbaI-digested pUC19, transformed into E.coli ER2502, and plated on LB agar plus Amp (100 µg/ml). Direct PCR of twelve colonies using pUC19 universal primers #1233 and #1224 (New England Biolabs) identified potential inverse PCR clones as follows: Individual colonies were picked from the LB agar plates, placed in 100 µl of dH$_2$O, boiled 5 minutes and then each allowed to cool to room temperature. Colony PCR conditions of 95° C. 10 sec, 62° C. 1', 72° C. 1', 30 cycles, were employed using 2.5 µl of boiled DNA in a 50 µl reaction with Vent® (Exo-) polymerase. Colonies with inserts were CsCl purified and sequenced with the same primers.

371 bp of new sequence was obtained from these inverse PCR clones. The extra 371 bp contained an ATG start codon and 55 subsequent codons of a new incomplete (ORF2) converging toward the original cloned ApoI fragment. The beginning of the snaBIR gene was not present. The rest of the new DNA from the HincII inverse PCR fragment was lost due to a newly discovered ApoI site in the adjacent chromosmal DNA. The 54 codons of ORF2 were found to be the truncated SnaBI control gene (snaBIC) at this newly discovered ApoI site. Since control genes usually precede endonuclease genes, we reasoned that snaBIR should be located downstream of snaBIC converging toward the original ApoI fragment containing the SnaBI methylase gene (snaBIM). A PCR primer (SninvAP) was then designed to PCR across this missing ApoI fragment back toward the original ApoI fragment containing snaBIM and the partial snaBIR (ORF1). PCR was carried out on *Sphaerotilus natans* genomic DNA using a newly designed primer (SninvAP) with (SnaBI2) primer:

5' GGCGCGGCATCAATGTTTGAATAC 3' (SninvAP) (SEQ ID NO:9)

5' TTCGGATCCCCGGGCTCTCGGAGCCAAT-CATTGCGC 3' (SnaBI2) (SEQ ID NO:10)

PCR conditions 95° C. 1' 54° C. 1', 72° C. 1', 30 cycles were employed using Vent® (Exo-) polymerase. A PCR fragment of approximately four hundred thirty (430) bp was obtained. It was digested with BamHI and ligated into SmaI- and BamHI-digested pUC19 followed by transformation into *E .coli* strain ER2502 and grown on LB agar plus Amp (100 μg/ml). Colony PCR of ten colonies using universal pUC19 primers #1233 and #1224 (New England Biolabs) with PCR conditions of 94° C. 10 sec, 62° C. 1', 72° C. 1', 30 cycles were employed using Vent® (Exo-) polymerase. Plasmid DNA from #8 contained the cloned PCR (430 bp) fragment and was CsCl purified and sequenced using the universal pUC19 primers. Sequencing revealing the remaining 24 aa of snaBIC, and the ATG codon and 40 aa of snaBIR. The complete snaBIR gene (ORF1) was found to be 672 bp in length and to code for a 223 aa protein of predicted MW of 24.5 kD (FIG. 3).

5. Sub-cloning the SnaBI methylase gene.

To clone the complete SnaBI endonuclease gene (snaBIR) an *E.coli* strain modified against SnaBI endonuclease digestion was made by cloning snaBIM into a compatible pACYC184 derivative, pIH919. The entire methylase gene (687 bp) was amplified from genomic DNA using Vent® polymerase with PCR conditions 95° C. 1' 54° C. 1', 72° C. 1', 30 cycles and two primers (SnaBI 5M) and (SnaBI 3M):

5'TGGCCCGGGAAGGAGGTTTAAAATAT-GTTTTACTACGGCAGAAAAAAACAAATCGC 3' (SnaBI 5M) (SEQ ID NO:11)

5'TTGCTGCAGTCACTACGCGACTAGCCT-GAGTTGCATGGC 3' (SnaBI 3M) (SEQ ID NO:12)

The PCR fragment was then digested at 37° C. for 2 hours with PstI and XmaI, then ligated at 17° C. for 2 hours into PstI and XmaI digested pIH919. The ligation was transformed into *E.coli* ER2267 and the transformed cells were plated on LB agar plus chloramphenicol (25 μg/ml). Colony PCR of eight colonies using universal pUC19 primer (#1233) and primer (SnaBI 5M) with PCR conditions of 94° C. 10 sec, 62° C. 1', 72° C. 1', 30 cycles were employed using Vent® (Exo-) polymerase. Two isolates, #3 and #8, contained the snaBIM PCR fragment. *E.coli* ER2502 containing #3 or #8 [snaBIM-pIH919] were made competent by the CaCl₂ method and transformed with pSnaBI-2; a pUC19 derivative containing two SnaBI sites. Plasmid DNA from four colonies for each was purified and incubated with SnaBI endonuclease. In all cases pSnaBI-2 was completely protected against SnaBI endonuclease digestion. #8 was then transformed into *E.coli* strain ER2683 and made competent using standard CaCl₂ method.

6. Sub-cloning the BsaAI methylase gene.

10 μg of bsaAIM-pUC19 plasmid containing a 1.9 kb EcoRI fragment was digested with 10 units of SspI at 37° C. for 60 minutes and gel purified. The bsaAIM-containing SspI fragment was ligated into the SmaI site of the CIP-treated vector pIH919 and then transformed into *E.coli* ER2502 and plated on LB agar plus chloramphenicol (25 μg/ml). Plasmid DNA was purified from sixteen colonies. One isolate, #8, was shown to fully protect against SnaBI endonuclease digestion indicating modification of SnaBI sites in vivo via expression of the BsaAI methylase gene. #8 was then transformed into ER2683 and made competent by CaCl₂ method.

7. Cloning of the complete SnaBI restriction endonuclease gene.

Two primers were synthesized for PCR amplification of the complete snaBIR (ORF1). The gene was amplified from genomic DNA using Vent® polymerase and PCR conditions of 95° C. 1' 54° C. 1', 72° C. 1', 30 cycles and two primers (SnaBI SR) and (SnaBI 3R):

5'TTGTTCTGCAGTAAGGAGGTTTAAAATATGCTG-AATTACAAGATTAATCCAGGACTC3' (SnaBI SR) (SEQ ID NO:13)

5'TTGGGATCCTCATGGAAATCTAAACCT-CAAGATTCTGGAGTACGC 3' (SnaBI 3R) (SEQ ID NO:14)

The PCR product was digested with PstI and BamHI and then gel purified followed by ligation into PstI- and BamHI-digested pRRS at 17° C. overnight. The ligation was transformed into ER2683 [pIH919-snaBIM] and ER2683 [pIH919-bsaAIM] and plated on LB agar plates plus Amp (100 μg/ml) and chloramphenicol (25 μg/ml). Plasmid DNA was purified by mini-preparation from 10 ml cell cultures from twelve colonies for each transformation. Although both *Ecoli* strains protected against SnaBI digestion, only ER2683 [pIH919-bsaAIM] cells yielded a clone containing the snaBIR PCR fragment with SnaBI endonuclease activity. One clone out of twelve isolates, #33 from ER2683 [pIH919-bsaAIM] transformation showed reduced endonuclease activity. ER2683 [pIH919-snaBIM] yielded no active SnaBI endonuclease clones by direct SnaBI chromosomal PCR of the snaBIR gene into pRRS.

The same PCR fragment using primers (SnaBI SR) and (SnaBI 3R) of snaBIR (ORF1) was also ligated at 17° C. overnight into gel purified pCAB16 digested with BsaAI followed by tranformation into ER2502 [pIH919-snaBIM] competent *E. coli* cells and plated on LB agar plates plus Amp (100 μg/ml) and chloramphenicol (25 μg/ml). Plasmid DNA was purified by mini-preparation from fifteen colonies and digested with PstI and Ba HI. Six isolates contained the PCR generated snaBIR fragment. Four clones #1, #2, #4, and #9 were sequenced. As previously described in the summary and detailed description, #1 and #9 contained the correct DNA sequence for snaBIR, however no detectable SnaBI endonuclease activity. All sequenced clones were in the opposite orientation to Plac and mspIR which might explain the lack of SnaBI endonuclease activity.

8. Expression of SnaBI endonuclease in *E. coli* strain ER2683 [pIH919-snaBIM].

Since #1 and #9 pCAB16-snaBIR clones contained PstI and BamHI sites designed within the PCR primers for snaBIR, both plasmids were digested with PstI and BamHI. The snaBIR insert was gel purified and ligated into PstI and BamHI digested pRRS inline with Plac. This ligation reaction was again transformed into ER2683 [pIH919-snaBIM] *E.coli* cells. Plasmid DNA from a total of 16 isolates were purified by mini-preparation, eight individual isolates from each #1 and #9 ligation. Plasmid DNA was digested with PstI and BamHI to indentify the snaBIR insert. Potential clones from each ligation were then assayed for SnaBI endonuclease activity. Only one isolate, #12, [from pCAB16–9, gel pure PstI/BamHI snaBIR +pRRS ligation], showed reduced activity of less than 5×10⁵ units per gram. This was the only clone with SnaBI endonuclease activity established in E.coli ER2683 [pIH919-snaBIM].

9. Expression of SnaBI endonuclease in E. coli strain ER2683 [pIH919-bsaAIM].

To overproduce SnaBI endonuclease from a clone required the use of the heterospecific methylase, M.BsaAI. As described in section 7, the entire SnaBI restriction endonuclease gene (672 bp) was amplified from genomic DNA, ligated at 17° C. overnight into gel purified pCAB16 linearized with BsaAI followed by tranformation into ER2502 [pIH919-snaBIM] competent E. coli cells and plated on LB agar plates plus Amp (100 μg/ml) and chloramphenicol (25 μg/ml). Isolated pCAB16-snaBIR clones #1 and #9 contained the correct DNA sequence for snaBIR were then digested with PstI and BamHI and gel purified, ligated into PstI- and BamHI-digested pRRS, followed by transformation into competent E.coli strain ER2683 [pIH919-bsaAIM] plated on LB agar plates plus Amp (100 μg/ml) and chloramphenicol (25 μg/ml). Plasmid DNA from twelve colonies from each transformation were isolated by mini-preparation for a total of twenty-four clones. All 24 clones appeared to contain the correct size insert; six clones from each plate were digested with PstI and BamHI and were found to contain the correct size snaBIR fragment. Six clones, #1, #2, #6, #13, #15, #18, displayed high activity for SnaBI endonuclease from overnight culture grown at 37° C. as follows: 50 ml Luria Broth plus Amp (100 μg/ml) and chloramphenicol (25 μg/ml) containing ER2683 [pIH919-bsaAIM, pRRS-snaBIR] culture were grown overnight at 37° C. Cells were harvested and resuspended in 4 ml sonication buffer (100 mM KCl, 10 mM Tris pH 7, 0.1 mM EDTA, 10 mM β-mercaptoethanol). Cells were lysed by sonication. Following centrifugation to remove debris the crude cell extract was assayed on T7 DNA for SnaBI endonuclease activity at 37° C. as follows: 1 μl crude extract was diluted one hundred fold (100 fold) in reaction buffer containing T7 DNA and mixed. 1 μl was tranferred to 50 μl mixed, 25 μl transferred through a series of six tubes incubated 15 minutes and 1 hr. SnaBI endonuclease activity yield is about 8×10⁶ units/gram of wet E.coli cells.

A sample of the E. coli containing ER2683 [pIH919-bsaAIM, pRRS-snaBIR], (NEB#1166) has been deposited under the terms and conditions of the Budapest Treaty with the American Type Culture Collection on Aug. 26, 1998 and received ATCC Accession Number 202166.

10. Purification of SnaBI restriction endonuclease.

The recombinant SnaBI restriction endonuclease is purified by standard protein purification techniques such as affinity chromatography, or ion-exhange chromatography.

What is claimed is:

1. Isolated DNA coding for the SnaBI restriction endonuclease, wherein the isolated DNA is obtainable from *Sphaerotilus natans*.

2. A recombinant DNA vector comprising a vector into which a DNA segment encoding the SnaBI restriction endonuclease has been inserted.

3. Isolated DNA encoding the SnaBI restriction endonuclease and methylase, wherein the isolated DNA is obtainable from ATCC NO. 15291.

4. A cloning vector which comprises the isolated DNA of claim 3.

5. A host cell transformed by the cloning vector of claims 2 or 4.

6. A method of producing SnaBI restriction endonuclease comprising culturing a host cell transformed with the vector of claims 2 or 4 under conditions suitable for expression of said endonuclease.

* * * * *

UNITED STATES PATENT AND TRADEMARK OFFICE

CERTIFICATE OF CORRECTION

PATENT NO.: 6,025,179            Page 1 of 2

DATED: February 15, 2000

INVENTOR(S): Keith D. Lunnen, Huimin Kong, Geoffrey G. Wilson

It is certified that errors appear in the above-identified patent and that said Letters Patent is hereby corrected as shown below:

In the Abstract
| | |
|---|---|
| Line 6 | after "in" delete "a" |
| Column 2, line 31 | replace "(1235-124)" with --(1235-1241)-- |
| Column 3, line 21 | replace "Bacterial" with --Bacteriol-- |
| Column 4, line 61 | replace "isolate the of" with --isolation of the-- |
| Column 5, line 36 | replace "Bacterial" with --Bacteriol-- |
| Column 6, line 52 | after "described" insert --in-- |
| Column 7, line 37 | delete "el," and insert --et al.-- |
| Column 7, line 39 | replace "a" with --an-- |
| Column 7, line 56 | replace "tranformation" with --transformation-- |
| Column 7, line 61 | replace "centifugation" with --centrifugation-- |
| Column 8, line 39 | after "95°C. 1'" insert --,-- |
| Column 8, line 43 | after "95°C. 1'" insert --,-- |
| Column 8, line 44 | replace "polymerase)" with --polymerase-- |
| Column 9, line 15 | after "95°C. 1'" insert --,-- |
| Column 9, line 39 | after "95°C. 1'" insert --,-- |
| Column 10, line 15 | after "95°C. 1'" insert --,-- |
| Column 10, line 44 | replace "tranformation" with --transformation-- |
| Column 11, line 14 | replace "tranformation" with --transformation-- |
| Column 11, line 19 | before "were" insert --and-- |
| Column 12, line 10 | after "debris" insert --,-- |

UNITED STATES PATENT AND TRADEMARK OFFICE

CERTIFICATE OF CORRECTION

PATENT NO.: 6,025,179

DATED: February 15, 2000

INVENTOR(S): Keith D. Lunnen, Huimin Kong and Geoffrey G. Wilson

It is certified that errors appear in the above-identified patent and that said Letters Patent is hereby corrected as shown below:

| | |
|---|---|
| Column 5, line 24 | replace "Sphaerotilus natans" with --*Sphaerotilus natans*-- |
| Column 7, line 2 | replace "bsaAIN" with --bsaAIM-- |
| Column 7, line 36 | replace "Sphaerotilus natans" with --*Sphaerotilus natans*-- |
| Column 7, line 52 | after "ori" insert --.-- |
| Column 10, line 17 | replace "(SnaBI SR)" with --(SnaBI 5R)-- |
| Column 10, line 19 | replace "(SnaBI SR)" with --(SnaBI 5R)-- |
| Column 10, line 41 | replace "(SnaBI SR)" with --(SnaBI 5R)-- |
| Column 10, line 48 | replace "Ba HI" with --BamHI-- |

Signed and Sealed this

Twenty-sixth Day of December, 2000

Attest:

Q. TODD DICKINSON

*Attesting Officer*     *Director of Patents and Trademarks*

SEQUENCE LISTING

<160> NUMBER OF SEQ ID NOS: 14

<210> SEQ ID NO 1
<211> LENGTH: 687
<212> TYPE: DNA
<213> ORGANISM: Sphaerotilus natans
<220> FEATURE:
<221> NAME/KEY: CDS
<222> LOCATION: (1)..(684)

<400> SEQUENCE: 1

```
atg ttt tac tac tac ggc aga aaa aaa caa atc gca aag cat tat ccg      48
Met Phe Tyr Tyr Tyr Gly Arg Lys Lys Gln Ile Ala Lys His Tyr Pro
 1               5                  10                  15 gct cca aat tat gga tgc ata att gag cca ttt gcg gga tcc gcc gcc      96
Ala Pro Asn Tyr Gly Cys Ile Ile Glu Pro Phe Ala Gly Ser Ala Ala
             20                  25                  30 tac tca ctc ttc tca ggc aac tgg cgc aat caa gtc gtt tta att gaa     144
Tyr Ser Leu Phe Ser Gly Asn Trp Arg Asn Gln Val Val Leu Ile Glu
         35                  40                  45 aaa gac ccc aaa gtc gca tcc att tgg gag tgg ttg ata agc gaa gcg     192
Lys Asp Pro Lys Val Ala Ser Ile Trp Glu Trp Leu Ile Ser Glu Ala
     50                  55                  60 act gaa caa aaa atc aaa aac ctg cca gac ctg aag gtt gga gaa aaa     240
Thr Glu Gln Lys Ile Lys Asn Leu Pro Asp Leu Lys Val Gly Glu Lys
 65                  70                  75                  80 agt tca gag ttc ctt cac att att cat gcg gcc aca aaa atg gca ttc     288
Ser Ser Glu Phe Leu His Ile Ile His Ala Ala Thr Lys Met Ala Phe
                 85                  90                  95 aaa tac aaa acc ata acg gtt acc cca gtt ttg gct aga aac tgg gaa     336
Lys Tyr Lys Thr Ile Thr Val Thr Pro Val Leu Ala Arg Asn Trp Glu
            100                 105                 110 att agc agg cgc gtt atg gcc gaa aac ctg caa aaa att aaa cat tgg     384
```

```
Ile Ser Arg Arg Val Met Ala Glu Asn Leu Gln Lys Ile Lys His Trp
            115                 120                 125 caa ata att tgc gga gac tac aca gtg gct cct gat att gag gct act        432
Gln Ile Ile Cys Gly Asp Tyr Thr Val Ala Pro Asp Ile Glu Ala Thr
        130                 135                 140 tgg ttt att gat ccg cca tac aag tca gag cca gga atg ggt tac ggc        480
Trp Phe Ile Asp Pro Pro Tyr Lys Ser Glu Pro Gly Met Gly Tyr Gly
145                 150                 155                 160 ttc agc agt gca ctt atc aac tac gag gaa ctg gca aaa tgg agc cta        528
Phe Ser Ser Ala Leu Ile Asn Tyr Glu Glu Leu Ala Lys Trp Ser Leu
                165                 170                 175 aac agg cag gga gaa gta att tgc tgc gag ggt gag tat ggc gac tac        576
Asn Arg Gln Gly Glu Val Ile Cys Cys Glu Gly Glu Tyr Gly Asp Tyr
            180                 185                 190 ctg cca ttt gaa act ctg ctg gat tta aag ggc gtt gcg gga aag tca        624
Leu Pro Phe Glu Thr Leu Leu Asp Leu Lys Gly Val Ala Gly Lys Ser
        195                 200                 205 agc agg gaa aaa ata ttt tac cgc acg cca cat tcg ccc atg caa ctc        672
Ser Arg Glu Lys Ile Phe Tyr Arg Thr Pro His Ser Pro Met Gln Leu
210                 215                 220 agg cta gtc gcg tag                                                    687
Arg Leu Val Ala
225

<210> SEQ ID NO 2
<211> LENGTH: 228
<212> TYPE: PRT
<213> ORGANISM: Sphaerotilus natans

<400> SEQUENCE: 2

Met Phe Tyr Tyr Tyr Gly Arg Lys Lys Gln Ile Ala Lys His Tyr Pro
1               5                   10                  15

Ala Pro Asn Tyr Gly Cys Ile Ile Glu Pro Phe Ala Gly Ser Ala Ala
            20                  25                  30

Tyr Ser Leu Phe Ser Gly Asn Trp Arg Asn Gln Val Val Leu Ile Glu
        35                  40                  45

Lys Asp Pro Lys Val Ala Ser Ile Trp Glu Trp Leu Ile Ser Glu Ala
    50                  55                  60

Thr Glu Gln Lys Ile Lys Asn Leu Pro Asp Leu Lys Val Gly Glu Lys
65                  70                  75                  80

Ser Ser Glu Phe Leu His Ile Ile His Ala Ala Thr Lys Met Ala Phe
                85                  90                  95

Lys Tyr Lys Thr Ile Thr Val Thr Pro Val Leu Ala Arg Asn Trp Glu
            100                 105                 110

Ile Ser Arg Arg Val Met Ala Glu Asn Leu Gln Lys Ile Lys His Trp
        115                 120                 125

Gln Ile Ile Cys Gly Asp Tyr Thr Val Ala Pro Asp Ile Glu Ala Thr
    130                 135                 140

Trp Phe Ile Asp Pro Pro Tyr Lys Ser Glu Pro Gly Met Gly Tyr Gly
145                 150                 155                 160

Phe Ser Ser Ala Leu Ile Asn Tyr Glu Glu Leu Ala Lys Trp Ser Leu
                165                 170                 175

Asn Arg Gln Gly Glu Val Ile Cys Cys Glu Gly Glu Tyr Gly Asp Tyr
            180                 185                 190

Leu Pro Phe Glu Thr Leu Leu Asp Leu Lys Gly Val Ala Gly Lys Ser
        195                 200                 205

Ser Arg Glu Lys Ile Phe Tyr Arg Thr Pro His Ser Pro Met Gln Leu
```

Arg Leu Val Ala
225

<210> SEQ ID NO 3
<211> LENGTH: 672
<212> TYPE: DNA
<213> ORGANISM: Sphaerotilus natans
<220> FEATURE:
<221> NAME/KEY: CDS
<222> LOCATION: (1)..(669)

<400> SEQUENCE: 3

```
atg ctg aat tac aag att aat cca gga ctc cat atc aat tgc gga ttt      48
Met Leu Asn Tyr Lys Ile Asn Pro Gly Leu His Ile Asn Cys Gly Phe
  1               5                  10                  15 att gtt act ggt gaa gcc gtc cgc aat gca ata atg caa acg aat gcc      96
Ile Val Thr Gly Glu Ala Val Arg Asn Ala Ile Met Gln Thr Asn Ala
             20                  25                  30 atc ctt ggg gac ttg ccg gca aat ttg tac aaa agc atc gac tac aaa     144
Ile Leu Gly Asp Leu Pro Ala Asn Leu Tyr Lys Ser Ile Asp Tyr Lys
         35                  40                  45 acg act agc gca atg att ggc tcc gtc ttt tgc gac agg ctt gct gat     192
Thr Thr Ser Ala Met Ile Gly Ser Val Phe Cys Asp Arg Leu Ala Asp
     50                  55                  60 gtg gtt ggg gca att gtt aat cct att gag aag ggg cat cct gat ttg     240
Val Val Gly Ala Ile Val Asn Pro Ile Glu Lys Gly His Pro Asp Leu
 65                  70                  75                  80 gtg cct cca gca gcg att aac tgc acc gaa gag gag tta cgg aac tac     288
Val Pro Pro Ala Ala Ile Asn Cys Thr Glu Glu Glu Leu Arg Asn Tyr
                 85                  90                  95 cca cag ggg ctg gaa atc aag tgc acc att ggc agc ata gaa act ggt     336
Pro Gln Gly Leu Glu Ile Lys Cys Thr Ile Gly Ser Ile Glu Thr Gly
            100                 105                 110 gca gac ttg cga gcg ggt caa acc cgc att gaa tcg ttg act gga atc     384
Ala Asp Leu Arg Ala Gly Gln Thr Arg Ile Glu Ser Leu Thr Gly Ile
        115                 120                 125 acg tgg cag gcc cat cac cgc gaa gtt gcc gaa ctg ctt ggt ttg gtt     432
Thr Trp Gln Ala His His Arg Glu Val Ala Glu Leu Leu Gly Leu Val
    130                 135                 140 tgg gat ttt ttt gaa gat ggc cgg gcc ttc aac tat cca gca atc agc     480
Trp Asp Phe Phe Glu Asp Gly Arg Ala Phe Asn Tyr Pro Ala Ile Ser
145                 150                 155                 160 ggg gcg ttt tat agc gat gat ctt tgc gag gat gat tgg gga caa atc     528
Gly Ala Phe Tyr Ser Asp Asp Leu Cys Glu Asp Asp Trp Gly Gln Ile
                165                 170                 175 agc gga acg aat ggt cgc aac aca aaa gtg agc gcg atg gtg gca agc     576
Ser Gly Thr Asn Gly Arg Asn Thr Lys Val Ser Ala Met Val Ala Ser
            180                 185                 190 gga aaa gca aaa atg ggt aga ggc tgg gtt gct gtg gtt gaa aaa gat     624
Gly Lys Ala Lys Met Gly Arg Gly Trp Val Ala Val Val Glu Lys Asp
        195                 200                 205 gaa tat tta aca gcg tac tcc aga atc ttg agg ttt aga ttt cca tga     672
Glu Tyr Leu Thr Ala Tyr Ser Arg Ile Leu Arg Phe Arg Phe Pro
    210                 215                 220
```

<210> SEQ ID NO 4
<211> LENGTH: 223
<212> TYPE: PRT
<213> ORGANISM: Sphaerotilus natans

<400> SEQUENCE: 4

-continued

```
Met Leu Asn Tyr Lys Ile Asn Pro Gly Leu His Ile Asn Cys Gly Phe
 1               5                  10                  15

Ile Val Thr Gly Glu Ala Val Arg Asn Ala Ile Met Gln Thr Asn Ala
             20                  25                  30

Ile Leu Gly Asp Leu Pro Ala Asn Leu Tyr Lys Ser Ile Asp Tyr Lys
         35                  40                  45

Thr Thr Ser Ala Met Ile Gly Ser Val Phe Cys Asp Arg Leu Ala Asp
     50                  55                  60

Val Val Gly Ala Ile Val Asn Pro Ile Glu Lys Gly His Pro Asp Leu
 65                  70                  75                  80

Val Pro Pro Ala Ala Ile Asn Cys Thr Glu Glu Leu Arg Asn Tyr
                 85                  90                  95

Pro Gln Gly Leu Glu Ile Lys Cys Thr Ile Gly Ser Ile Glu Thr Gly
             100                 105                 110

Ala Asp Leu Arg Ala Gly Gln Thr Arg Ile Glu Ser Leu Thr Gly Ile
         115                 120                 125

Thr Trp Gln Ala His His Arg Glu Val Ala Glu Leu Leu Gly Leu Val
     130                 135                 140

Trp Asp Phe Phe Glu Asp Gly Arg Ala Phe Asn Tyr Pro Ala Ile Ser
145                 150                 155                 160

Gly Ala Phe Tyr Ser Asp Asp Leu Cys Glu Asp Asp Trp Gly Gln Ile
                 165                 170                 175

Ser Gly Thr Asn Gly Arg Asn Thr Lys Val Ser Ala Met Val Ala Ser
             180                 185                 190

Gly Lys Ala Lys Met Gly Arg Gly Trp Val Ala Val Glu Lys Asp
         195                 200                 205

Glu Tyr Leu Thr Ala Tyr Ser Arg Ile Leu Arg Phe Arg Phe Pro
     210                 215                 220

<210> SEQ ID NO 5
<211> LENGTH: 240
<212> TYPE: DNA
<213> ORGANISM: Sphaerotilus natans
<220> FEATURE:
<221> NAME/KEY: CDS
<222> LOCATION: (1)..(237)

<400> SEQUENCE: 5 atg aac tca ctg agt acc gcc ata gcc caa gcg tta gtc aaa tat cgt      48
Met Asn Ser Leu Ser Thr Ala Ile Ala Gln Ala Leu Val Lys Tyr Arg
 1               5                  10                  15 cat ttg tca cac ctc tct caa gag gag ctt gcc gat gct gct ggc att      96
His Leu Ser His Leu Ser Gln Glu Glu Leu Ala Asp Ala Ala Gly Ile
             20                  25                  30 cat aga acc tat gtg agt cag ata gag cgc ggg cta aag atg ccc act     144
His Arg Thr Tyr Val Ser Gln Ile Glu Arg Gly Leu Lys Met Pro Thr
         35                  40                  45 gtc gcc att ctt ttt aaa att tcc aag gcg ctg aat att cga gca agc     192
Val Ala Ile Leu Phe Lys Ile Ser Lys Ala Leu Asn Ile Arg Ala Ser
     50                  55                  60 gac ttg att ggt gag att gaa ggt cag tat gct gaa tta caa gat taa     240
Asp Leu Ile Gly Glu Ile Glu Gly Gln Tyr Ala Glu Leu Gln Asp
 65                  70                  75

<210> SEQ ID NO 6
<211> LENGTH: 79
<212> TYPE: PRT
<213> ORGANISM: Sphaerotilus natans
```

<400> SEQUENCE: 6

Met Asn Ser Leu Ser Thr Ala Ile Ala Gln Ala Leu Val Lys Tyr Arg
1               5                   10                  15

His Leu Ser His Leu Ser Gln Glu Glu Leu Ala Asp Ala Ala Gly Ile
            20                  25                  30

His Arg Thr Tyr Val Ser Gln Ile Glu Arg Gly Leu Lys Met Pro Thr
        35                  40                  45

Val Ala Ile Leu Phe Lys Ile Ser Lys Ala Leu Asn Ile Arg Ala Ser
    50                  55                  60

Asp Leu Ile Gly Glu Ile Gly Gln Tyr Ala Glu Leu Gln Asp
65                  70                  75

<210> SEQ ID NO 7
<211> LENGTH: 33
<212> TYPE: DNA
<213> ORGANISM: Sphaerotilus natans

<400> SEQUENCE: 7
ttctctagaa gcttgggagc gggtcaaacc cgc                              33

<210> SEQ ID NO 8
<211> LENGTH: 36
<212> TYPE: DNA
<213> ORGANISM: Sphaerotilus natans

<400> SEQUENCE: 8
ttcggatccc cgggctctcg gagccaatca ttgcgc                           36

<210> SEQ ID NO 9
<211> LENGTH: 24
<212> TYPE: DNA
<213> ORGANISM: Sphaerotilus natans

<400> SEQUENCE: 9
ggcgcggcat caatgtttga atac                                       24

<210> SEQ ID NO 10
<211> LENGTH: 36
<212> TYPE: DNA
<213> ORGANISM: Sphaerotilus natans

<400> SEQUENCE: 10
ttcggatccc cgggctctcg gagccaatca ttgcgc                           36

<210> SEQ ID NO 11
<211> LENGTH: 56
<212> TYPE: DNA
<213> ORGANISM: Sphaerotilus natans

<400> SEQUENCE: 11
tggcccggga aggaggttta aaatatgttt tactacggca gaaaaaaaca aatcgc     56

<210> SEQ ID NO 12
<211> LENGTH: 40
<212> TYPE: DNA
<213> ORGANISM: Sphaerotilus natans

<400> SEQUENCE: 12
ttgctgcagt cactacgcga ctagcctgag ttgcatgggc                       40

-continued

```
<210> SEQ ID NO 13
<211> LENGTH: 57
<212> TYPE: DNA
<213> ORGANISM: Sphaerotilus natans

<400> SEQUENCE: 13
ttgttctgca gtaaggaggt ttaaaatatg ctgaattaca agattaatcc aggactc      57

<210> SEQ ID NO 14
<211> LENGTH: 45
<212> TYPE: DNA
<213> ORGANISM: Sphaerotilus natans

<400> SEQUENCE: 14
ttgggatcct catggaaatc taaacctcaa gattctggag tacgc                   45
```